United States Patent [19]

Vasquez et al.

[11] Patent Number: 4,739,039
[45] Date of Patent: Apr. 19, 1988

[54] METHOD FOR PREPARING ANTIHEMOPHILIC FACTOR (AHF) BY COLD PRECIPITATION AND FOR IMPROVING SOLUBILITY OF RECOVERED AHF PRODUCT

[75] Inventors: Rodolfo A. Vasquez, Norwalk; Maria E. Co-Sarno, Cerritos; Clifford R. Graf, Lakeview Terrace, all of Calif.

[73] Assignee: Baxter Travenol Laboratories, Inc., Deerfield, Ill.

[21] Appl. No.: 73,380

[22] Filed: Jul. 15, 1987

Related U.S. Application Data

[63] Continuation of Ser. No. 796,559, Nov. 8, 1985, abandoned.

[51] Int. Cl.$^4$ .............................................. A61K 35/14
[52] U.S. Cl. ................................... 530/383; 424/101; 514/2; 514/834
[58] Field of Search ........................ 530/383; 424/101; 514/2, 834

[56] References Cited

U.S. PATENT DOCUMENTS

| | | | |
|---|---|---|---|
| 4,069,216 | 1/1978 | Shanbrom | 530/383 |
| 4,104,266 | 8/1978 | Wickerhauser | 530/383 |
| 4,289,691 | 9/1981 | Rock et al. | 530/383 |
| 4,294,826 | 10/1931 | Feldman | 424/101 |
| 4,386,068 | 5/1983 | Mitra et al. | 424/101 |
| 4,387,092 | 6/1983 | Liautaud et al. | 424/101 |
| 4,404,131 | 9/1983 | Schwartz et al. | 530/383 |
| 4,406,886 | 9/1983 | Bier et al. | 424/101 |
| 4,455,301 | 6/1984 | Mitra et al. | 424/101 |
| 4,543,210 | 9/1985 | Mitra et al. | 424/101 |

FOREIGN PATENT DOCUMENTS 2636757  2/1978  Fed. Rep. of Germany .
1507198  4/1978  United Kingdom .

OTHER PUBLICATIONS

Pool and Hershgold, High-potency Antihaemophilic Factor Concentrate etc., Nature, vol. 203, p. 312, Jul. 18, 1964.
Smith et al., A Factor VIII Concentrate of Intermediate Purity etc., Transfusion, vol. 19, No. 3, May-Jun. 1979.
Wickerhauser et al., Development of Large-Scale Fractionation Methods, Vox Sang., 35, pp. 18 to 31 (1978).
Rock et al., Intermediate Purity Factor VIII Production etc., Thrombosis Research, vol. 18, pp. 551-556 (1980).
Marguerie, The Binding of Calcium to Fibrinogen: etc., Biochimica et Biophysica Acta, 494, 172-181 (1977).
Mikaelsson et al., Human Factor VIII: A Calcium-Linked Protein Complex, Blood, vol. 62, No. 5, pp. 1006-1015 (1983).

Primary Examiner—Delbert R. Phillips
Assistant Examiner—Nathan M. Nutter
Attorney, Agent, or Firm—Robert Hartenberger; Marjorie Hunter; Paul Flattery

[57] ABSTRACT

An improved method of recovering antihemophilic factor (AHF) from cryoprecipitated blood plasma is provided. The improved method incorporates the addition of a calcium ion source during the step of cold precipitation of fibrinogen and fibronectin contaminants, as well as the addition of polyethylene glycol (PEG) at one of various stages of the recovery process. PEG may be added during the cold precipitation of fibrinogen and fibronectin, during the precipitation of AHF, or prior to the filtration of AHF solution. The method of the present invention results in a final AHF product having greatly increased solubility, higher specific activity, and lower fibrinogen and fibronectin content.

36 Claims, No Drawings

METHOD FOR PREPARING ANTIHEMOPHILIC FACTOR (AHF) BY COLD PRECIPITATION AND FOR IMPROVING SOLUBILITY OF RECOVERED AHF PRODUCT

This application is a continuation of application Ser. No. 06/796,559, filed 11/08/85 and now abandoned

BACKGROUND OF THE INVENTION

This invention relates to a method for purification and/or concentration of antihemophilic factor (AHF). More particularly, this invention relates to a method for improving the final AHF product recovered from cryoprecipitated blood plasma using cold precipitation.

The process of blood coagulation is a complicated biological activity and involves the interaction of several substances found in normal whole blood. It is known that certain factors associated with the blood coagulation mechanism are absent or seriously deficient in certain individuals. For example, classical hemophilia (hemophilia A) is a disease caused by a deficiency of AHF (Factor VIII). In individuals suffering from the congenital hemophilia known as hemophilia B, the blood is deficient in plasma thromboplastin component (PTC, Factor IX). Several other factors which are important in the coagulation mechanism are Factors II, VII and X.

In the past, treatment of hemophiliacs consisted of transfusing the patient with whole blood or blood plasma. Better medical practice dictates that, whenever possible, the patient be administered only those blood components in which he is deficient. Due to the universal shortage of blood, it is also advantageous to fractionate blood into its various components, whereby individual components can be used for patient treatment as required.

Various methods of fractionating blood and blood plasma into its separate components or concentrates thereof are known. The work on development of the alcohol fractionation method is particularly noteworthy. With specific reference to the production of AHF, recent U.S. Pat. Nos. 4,383,989; 4,386,068; 4,387,092; 4,445,301 and 4,404,131 illustrate improved methods of obtaining a highly purified concentrate of AHF.

Unfortunately, there are a number of problems associated with the isolation of AHF. AHF is a glycoprotein that closely associates itself with other proteins in blood plasma, such as fibrinogen and fibronectin. Fibrinogen and fibronectin are considered contaminants in the final AHF solution. Therefore, it is necessary to precipitate out of the plasma as much fibrinogen and fibronectin as possible while maintaining a high specific activity of AHF in the final product. It is also desirable to obtain as high a yield of AHF as possible from the initial blood plasma due to the rarity and expense of whole blood. It is further advantageous to have a final AHF product with high solubility, because a low solubility of AHF requires the administration of large amounts of fluid to a patient. Large quantities of fluid are both a strain on the heart and circulation of the patient and make the hemophilia patient dependent on the continual substitution of the missing blood factors or infusions, as well as requiring the assistance of physicians for administration. High fibrinogen and fibronectin contect in the final product results in lower solubility than is desired.

Various methods are known in the art for isolating AHF, but these methods are often extremely expensive to perform and do not provide an optimum combination in the final AHF product of high solubility, low fibrinogen and fibronectin content, high specific activity of AHF and high yield of AHF from the initial blood plasma. What is needed therefore, is a method isolating AHF which meets all of these criteria and is not prohibitively expensive. The present invention satisfies these needs and provides other related advantages.

SUMMARY OF THE INVENTION

The present invention resides in a method of isolating AHF from a cryoprecipitate solution of blood plasma by cold precipitation of contaminants, including fibrinogen and fibronectin, and subsequent recovery of AHF from the resulting supernate solution. The addition of a calcium ion source to the cryoprecipitate during the initial cold precipitation step aids in the desired precipitation of fibrinogen and fibronectin, while the addition of polyethylene glycol (PEG) at one of the various stages in the process greatly increases the solubility of the final AHF product and may also serve to lower the fibrinogen and fibronectin content, depending on when the PEG is added. The resulting AHF product has fewer contaminants, greater solubility and a higher specific activity than AHF products isolated by other methods.

The method of the present invention involves forming a cryoprecipitate from frozen plasma. The cryoprecipitate is dissolved in distilled water to form a solution of low ionic strength. A source of calcium ion, preferably calcium chloride, is added, but only in sufficient quantity to bring the calcium ion concentration to a non-activating strength. Any calcium salt may be used as a source of calcium ion as long as the calcium salt is soluble and the anion portion of the salt is non-toxic and is not a chelator. Fibrinogen and fibronectin are then precipitated by adjusting the pH and lowering the temperature of the solution while mixing. The AHF is then recovered from the resulting supernate by precipitation and filtration.

After precipitation of the fibrinogen and fibronectin, the mixture obtained is centrifuged and the precipitate discarded. The pH of the supernate is first adjusted and then is concentrated to a specific weight/volume% (w/v %) by ultrafiltration. Upon adjusting the sodium concentration of the solution by the addition of sodium chloride and further adjustment of the pH, the temperature of the solution is adjusted to approximately 8° C. Glycine is then added and the temperature is again adjusted, downward to approximately 2° C. to precipitate the AHF. The mixture is centrifuged and the AHF precipitate is suspended in citrated saline with subsequent adjustment of pH. After filtration, the solution is diluted to the desired potency and again filtered, to yield a bulk AHF solution. The bulk AHF solution is then dispensed into final containers, frozen, lyophilized and heated. The final AHF product is stored at approximately 5° C.

PEG may be added at various stages of the recovery process, with varying results. If PEG is added just before the final filtration step, the major benefit will be an increase in solubility. As long as PEG is added at some point during the recovery process, it will be present in the final AHF solution, and solubility will be increased.

PEG may alternatively be added just before the glycine addition step. Addition of PEG at this point assists in precipitation of AHF from the supernate solution, as well as providing increased solubility of the final AHF product.

PEG may alternatively be added during the initial cold precipitation step, between the pH and temperature adjustment steps. The amount of PEG added at this point in the process must be carefully controlled so as not to precipitate out the AHF along with the fibrinogen and fibronectin. When PEG is added during the cold precipitation, adjustments should be made to the subsequent AHF recovery steps. Specifically, concentration of the resultant supernate solution should be to a lower weight/volume percent, depending on the amount of PEG added, and the sodium concentration should be adjusted to a higher level for optimum results. Of the three different stages of the process during which PEG may be added, the latter two are preferred, since they provide decreased fibrinogen and fibronectin content in the final product as well as increased solubility of the final product.

Other features and advantages of the present invention will become apparent from the following detailed description, which illustrates, by way of example, the principles of the invention.

DETAILED DESCRIPTION OF THE PREFERRED EMBODIMENT

The present invention is embodied in a process for recovering AHF from cryoprecipitated blood plasma. The process generally involves cold precipitation of the cryoprecipitate to precipitate out contaminant proteins such as fibrinogen and fibronectin, followed by recovery of AHF from the resulting supernate solution by precipitation and filtration. Addition of a calcium ion source during the cold precipitation step increases the precipitation of fibrinogen and fibronectin, thereby lowering the final concentration of these contaminants in the final AHF product. Polyethylene glycol (PEG) added at one of the stages of the recovery process will increase solubility of the final AHF product. Depending on which stage of the recovery process the PEG is added it will also assist in precipitation of the fibrinogen and fibronectin or the AHF. The present method advantageously yields a final AHF product with high solubility, high specific activity, low fibrinogen and fibronectin concentration and high yield.

More specifically, the method of the present invention involves starting with bottles of frozen plasma. As set forth in Example 1, cryoprecipitate is collected from frozen plasma by thawing in a controlled environment, in accordance with techniques known in the art.

The cryoprecipitate is dissolved in water for injection at 20° C.-35° C., preferably about 23° C. Sufficient calcium chloride is added to provide a minimum calcium concentration of between 0.001 mM and 1.0 mM. The pH is adjusted to approximately 6.5±0.2 and the solution is cooled to between 5° C. and 15° C. while mixing.

The resulting precipitate, containing the fibrinogen and fibrinectin contaminants, is removed by centrifugation. The pH of the supernate containing the AHF is adjusted to 7.0±0.2 and is concentrated by ultrafiltration to a protein concentration of between 1.0 w/v % and 4.0 w/v %. The ultrafiltration units used are polysulfone or equivalent membranes, having nominal molecular weight cutoffs of 100,000.

After ultrafiltration, the retentate is adjusted to a sodium concentration of about 150 to 800 mEq/liter with sodium chloride and the pH is adjusted to 7.3±0.2 with sodium hydroxide. 1.0 to 11.0 grams of PEG are added per liter of solution. The solution is then cooled to 8° C.±0.5° C. and glycine is added to a concentration of between 1.3 M and 2.5 M. The temperature of the solution is adjusted to 2° C.±2° C. while mixing to precipitate out the AHF.

The resulting solution is centrifuged and the precipitate, now containing the AHF, is suspended in citrated saline buffer (0.12 M sodium chloride and 0.2 M sodium citrate) and diluted to the desired AHF activity. The pH is adjusted to 6.8±0.2 and the solution is clarified by filtration. The solution is readjusted to the desired AHF activity, if necessary, and sterilized by filtration.

The resulting bulk solution is then dispensed into final containers, frozen, lyophilized and sealed under aseptic conditions. The sealed vials are then heated to reduce viral risk.

The results of the AHF recovery process used in Example 1 are shown in Table 1. As seen in that table, the solubility of the final AHF product was 53 seconds in non-heated form and 64 seconds in heated form. By comparison, in Table 5, the solubility of AHF prepared by the same process, without the addition of PEG, was 351 seconds, and 492 seconds after heating. Moreover, as shown in Table 1, the fibrinogen content of the final AHF product was 418 mg/dL, a relatively low level, while the specific activity of the AHF was 3.40 u/mg protein, a desireably high level.

The source of calcium ions added during the cold precipitation step may be any calcium salt, as long as the salt is soluble and the anion portion is non-toxic and is not a chelator. Examples of toxic calcium salts that could not be used would be calcium fluoride and calcium bromide. Examples of chelators that could not be used are calcium citrate and calcium oxalate. By example, and not by way of limitation, calcium salts that may be used in addition to calcium chloride are calcium carbonate and calcium gluconate.

Addition of calcium gluons during the cold precipitation step results in increased precipitation of the fibrinogen and fibronectin contaminants. However, a limited amount of calcium salt must be added so that the solution remains non-reactive. A reactive solution would result in clotting, which would render the solution useless.

Instead of adding PEG during the AHF precipitation step as in Example 1, PEG may be added during the cold precipitation of the fibrinogen and fibronectin, as shown in Examples 2-4. Example 2 and Table 2 show the general advantage of using PEG during the cold precipitation step. In Example 2A, the AHF recovery process was performed using the basic process set forth above, the same as was used in Example 1, with the same proportions and percentages of reagents and solutions and different absolute volumes and weights, but with no addition of PEG anywhere in the AHF recovery process. In Example 2B, the AHF recovery process was again performed in substantially similar fashion to Example 1, but instead of the addition of 0.9 w/v % PEG during the AHF precipitation step, 0.25 w/v % PEG was added between the pH adjustment and temperature adjustment steps in the cold precipitation stage of the process. The ultrafiltration concentration and the sodium concentration adjustment were performed the same as in Example 1, the concentration being done to 3.0 w/v % and the sodium concentration being adjusted to 160 mEq/L. A comparison of the results that appear in Table 2 shows the dramatic improvement in both specific activity and fibrinogen content of the AHF product. The tests that yielded the results shown in Table 2 were performed on the bulk AHF sample, just before filling, freezing, and lyophilization. The specific activity of the PEG sample was 3.21 u/mg protein, while the specific activity of the sample without PEG was only 2.38 u/mg protein. Similarly, the fibrinogen content of the sample without PEG was 1,279.6 mg%, while the fibrinogen content of the PEG sample was a substantially lower 937.4 mg%.

While the process of the present invention can be carried out using 0.25% PEG during the cold precipitation step and no adjustment of the sodium concentration during the AHF precipitation step, the addition of PEG during the cold precipitation step results in a lower protein concentration in the supernate, which suggests an alternate sodium concentration adjustment. Thus, in Example 3, the AHF recovery process was performed the same as in Example 2, but with the sodium concentration during the AHF precipitation step being adjusted to 600 mEq/L rather than 160 mEq/L. The results, shown in Table 3, derived from tests on the bulk AHF just before filling, freezing and lyophilization, show improvements in both the specific activity and fibrinogen content of the AHF sample, which were 3.48 u/mg and 565.1 mg% respectively. Generally, the sodium concentration during the AHF precipitation step can be adjusted within a range of 150 mEq/L to approximately 800 mEq/L.

The addition of a higher concentration of PEG during the cold precipitation step provides even more advantageous results, as shown in Example 4 and Table 4. In Example 4, 0.5 g % of PEG was added during the cold prcipitation step, instead of the 0.25 g % added in Example 3. Concentrations and steps throughout the rest of the process remained the same, including adjustment of the sodium concentration during the AHF precipitation step to 600 mEq/L, except that the AHF solution during the AHF precipitation step was concentrated to only 2.0 w/v % rather than 3.0 w/v %. At higher percentages of PEG added during the cold precipitation of fibrinogen and fibronectin, the concentration of AHF solution during the AHF precipitation step should be reduced for optimum results. The results of tests performed on the bulk AHF, shown in Table 4, reveal a specific activity of the AHF product of 5.04 u/mg and a fibrinogen content of 281 mg%, both even better than the results obtained in Example 3.

The presence of PEG of the final AHF product improves the solubility of the AHF product. Strictly from a solubility standpoint, it does not matter when the PEG is added because its presence will remain throughout the process through to the final AHF product. Example 5 and Table 5 demonstrate the effect of PEG's presence in the final AHF product on solubility. The tests performed in Example 5 included the addition of 0.2 g % PEG to the AHF precipitated solution just after the dilution to desired potency and just before the sterile filtration steps during the final filtration process. Table 5 shows the results of a comparison between the method used in Example 5 and the method used in Example 2B, the same method without the addition of PEG. The solubility of the AHF product containing PEG was 301 seconds before heating, as compared with 351 seconds for the AHF solution with no PEG added. Similarly, the solubility of the PEG solution after heating was 234 seconds as compared with 492 seconds for the solution containing no PEG additive. Of course, while adding PEG to the solution at this stage is advantageous as compared with no addition of PEG, the benefits of increased precipitation of fibrinogen and fibronectin will not be realized as in Examples 2–4, where the PEG is added during the cold precipitation step. Therefore, the methods shown in Examples 2, 3 and 4 are preferred, with the method shown in Example 4 being most preferred.

While the advantage of the addition of PEG at various stages in the AHF recovery process have been illustrated, it should be emphasized that the method described in Example 2B, without PEG addition, but with the addition of a calcium ion source to the dissolved cryoprecipitate during the cold precipitation step is itself a significant advance over current AHF recovery techniques known in the art.

The following examples will serve to illustrate the present invention in accordance with the embodiments discussed herein.

EXAMPLE 1

751 liters of frozen plasma were thawed in a controlled environment in accordance with techniques known in the art. The thawed plasma was pumped directly to the centrifuge. After centrifugation, the cryo-poor plasma was collected in a jacketed stainless steel reaction tank.

The resulting cryoprecipitate, 6.0 Kg, was dissolved in 24 Kg water at 23° C. 2.4 Kg of 0.68 mM calcium chloride solution was added to provide a minimum calcium concentration of 50 uM. The pH of the solution was adjusted to 6.5 by addition of 110 ml of acetic acid. The solution was then cooled in a circulating water bath to 9° C. while mixing.

The resulting precipitate was removed by centrifugation in a Beckman model J6B bucket centrifuge. The pH of the supernate was adjusted to 7.0 by addition of 37 ml NaOH and the solution was concentrated by ultrafiltration to a protein concentration of 3 w/v %. The ultrafiltration units used were Polysulfone membranes with a nominal molecular weight cut-off of 100,000.

After the ultrafiltration, the retentate was adjusted to a sodium concentration of 160 mEq/L by addition of 49.4 g NaCl. The pH was then adjusted to 7.3 by addition of 7 ml of 1 N sodium hydroxide. 60g of PEG (9.0 g/L) were added and the solution was cooled in a circulating water bath to 8° C. 0.85 Kg of glycine was added so that the concentration was 1.7 M. The temperature of the solution was then adjusted to 2° C. in a circulating water bath while mixing.

The resulting solution was centrifuged in a Beckman centrifuge and the precipitate was suspended in 1.9 Kg citrated saline buffer (0.12 M sodium chloride and 0.02 M sodium citrate) to dilute the solution to 60 AHF units/ml. The pH of the solution was adjusted to 6.8 by addition of 2 ml of 1N acetic acid and the solution was clarified by filtration. The solution was readjusted to an AHF activity of 40 AHF units/ml by addition of 3 liters of citrated saline buffer and the resulting solution was sterilized by filtration.

The resulting 7.8 liters of bulk AHF solution were dispensed into 30 ml containers, 10 ml of AHF solution being placed in each container. The containers were then frozen, lyophilized and heat treated.

TABLE 1

Test Results of AHF Product Obtained In Example 1

| Property Tested | Non-Heated | Heated |
|---|---|---|
| AHF potency, u/ml | 34 | 33 |
| AHF related antigen, u/ml | 53 | 49 |
| AHF coagulant antigen, u/ml | 46 | 43 |
| Fibrinogen, mg/dL | | |
| biological | 414 | 418 |
| immunological | 502 | 501 |
| Solubility, sec | 53 | 64 |
| Fibronectin, mg/ml | 4.0 | 3.5 |
| Fill volume, ml | — | 10 |
| Total protein, g container | — | 0.1 |
| Moisture, percent | — | 1.2 |
| pH | — | 6.8 |
| Polyethylene glycol, g/100 ml | — | 0.06 |
| Glycine, M | — | 0.18 |
| Specific Activity, AHF units/mg protein | — | 3.40 |

EXAMPLE 2A

Recovery of AHF was performed using the same process as is set forth in Example 1, with the same proportions and percentages of reagents in solutions, but with different absolute volumes and weights of materials. However, the addition of 9.0 g of PEG per liter of solution during the AHF precipitation step was not performed. No PEG was added throughout the AHF recovery process.

EXAMPLE 2B

Recovery of AHF was performed using the same process as is set forth in Example 1, with the same proportions and percentages of reagents in solutions, but with different absolute volumes and weights of materials. However, instead of the addition of 9.0 g of PEG per liter of solution during the AHF precipitation step, 0.25 g% PEG was added between the steps of pH adjustment to 6.5 and the temperature adjustment to 9° C. during the initial cold precipitation of fibrinogen and fibronectin step.

The results of specific activity and fibrinogen content tests of the products recovered in Examples 2A and 2B appears in Table 2.

TABLE 2

Test Results of AHF Products Obtained in Examples 2A and 2B

| Property | Without PEG | With 0.25 g % PEG |
|---|---|---|
| Fibrinogen, mg % | 1279.6 | 937.4 |
| Specific activity, AHF units/mg protein | 2.38 | 3.21 |

EXAMPLE 3

AHF was recovered as set forth in Example 2B, except that the sodium concentration was adjusted to 600 mEq/L rather than 160 mEq/L during the AHF precipitation step. The bulk AHF solution was tested, just before it was filled, frozen, and lyophilized. The results appear in Table 3.

TABLE 3

Results of Testing Performed on Bulk AHF Solution Obtained In Example 3

| Property | Value |
|---|---|
| Fibrinogen, mg % | 565.1 |
| Specific activity, AHF units/mg protein | 3.48 |

EXAMPLE 4

AHF was recovered as set forth in Example 3, except that 0.50 g % PEG was added during the cold precipitation step rather than 0.25 g % PEG, and the solution during the AHF precipitation step was concentrated to only 2.0 w/v % total protein rather than 3.0 w/v % total protein. As in Example 3, the sodium concentration during the AHF precipitation step was adjusted to 600 mEq/L. Results of tests performed on the bulk AHF solution obtained in Example 4 appear in Table 4.

TABLE 4

Results of Testing Performed on Bulk AHF Solution Obtained In Example 4

| Property | Value |
|---|---|
| Fibrinogen, mg % | 281 |
| Specific activity, AHF units/mg protein | 5.04 |

EXAMPLE 5

AHF was recovered as set forth in Example 2A, except that instead of adding 0.25 g % PEG during the cold precipitation step, 0.2 g % PEG was added to the AHF precipitated solution just after the dilution to the desired potency and just before the sterile filtration steps were performed during the final filtration process. Another AHF recovery test was then performed in similar fashion with the addition of 0.1 g % PEG instead of 0.2 g % PEG. Two other AHF recovery tests were also conducted, as set forth in Example 2B, with no PEG added at any stage of the recovery process.

The results of solubility tests on the products obtained in the four different experiments conducted in Example 5, both before heating the lyophilized product and after heating the lyophilized product, are shown in Table 5.

TABLE 5

Results of Solubility Tests Conducted on AHF Products Obtained In Example 5

| Lot No. Treatment | Solubility Before Heating (Secs.) | Solubility After Heating (Secs.) |
|---|---|---|
| 2830X364 No additive | 351 | 492 |
| 2830X364 + 0.2 g % PEG | 301 | 234 |
| 2830A012 No additive | — | 428 |
| 2830A012 + 0.1 g % PEG | — | 97 |

The preceding examples and description are provided to assist in understanding the present invention and are exemplary only. They are not intended to limit the present invention in any way. Others skilled in the art will recognize that other methods and/or materials may be used, depending on particular circumstances, and still remain within the scope and spirit of the present invention. Accordingly, the present invention is not intended to be limited, except as by the appended claims.

What is claimed is:

1. A method for purifying and concentrating AHF from blood plasma or plasma fractions comprising:
   (a) dissolving cryoprecipitated blood plasma in water to form a solution having low ionic strength;
   (b) adding a source of calcium ion to adjust the concentration of ionized calcium in the solution to a non-activating concentration;
   (c) adjusting the pH of the solution to from about 6.0 to about 7.0;
   (d) adjusting the temperature of the solution to from about 5° C. to about 15° C. for a period of time sufficient to form a precipitate and supernate solution that contains said AHF;
   (e) recovering said AHF containing supernate; and
   (f) recovering said AHF from said AHF containing supernate;

2. The method as set forth in claim 1 wherein the water in which said cryoprecipitated blood plasma is dissolved is at a temperature of from about 20° C. to about 35° C.

3. The method as set forth in claim 2 wherein the temperature of said water is about 23° C.

4. The method as set forth in claim 1 wherein said source of calcium ion is a calcium salt.

5. The method as set forth in claim 4 wherein said calcium salt is calcium chloride.

6. The method as set forth in claim 5 wherein said concentration of calcium chloride added to the solution is from about 0.001mM to about 1.0mM.

7. The method as set forth in claim 6 wherein said calcium chloride concentration added to the solution is about 0.05mM.

8. The method as set forth in claim 1 wherein the pH of the solution is adjusted in step (c) to about 6.5.

9. The method as set forth in claim 1 wherein the temperature of the solution is adjusted in step (d) to about 9° C.

10. The method as set forth in claim 1 wherein steps (e) and (f) comprise:
    (a) separating said precipitate from said AHF containing supernate;
    (b) concentrating said AHF containing supernate solution to a desired level of total protein;
    (c) adjusting the sodium concentration of said AHF supernate solution to a desired level;
    (d) adding glycine as a precipitant to said AHF containing supernate solution to obtain a desired glycine concentration;
    (e) adjusting the temperature of said AHF supernate solution to a desired level to control the formation of a precipitate that contains said AHF; and
    (f) recovering said AHF from said precipitate.

11. The method as set forth in claim 10 wherein said separation in step (a) is performed by centrifugation or filtration.

12. The method as set forth in claim 10 wherein said concentration in step (b) is performed by ultrafiltration.

13. The method as set forth in claim 10 wherein said desired concentration level is from about 1.0 w/v % total protein to about 4.0 w/v % total protein.

14. The method as set forth in claim 13 wherein said desired concentration level is about 2.5 w/v % total protein to about 3.0 w/v % total protein.

15. The method as set forth in claim 10 wherein said sodium concentration is adjusted in step (c) to from about 150 mEq/liter to about 800 mEq/liter.

16. The method as set forth in claim 15 wherein said sodium concentration is adjusted in step (c) to about 160 mEq/liter.

17. The method as set forth in claim 10 wherein the desired concentration of glycine in step (d) is about 1.3 M to about 2.5 M.

18. The method as set forth in claim 17 wherein the desired level of glycine concentration in step (d) is about 1.7 M.

19. The method as set forth in claim 10 wherein the temperature is adjusted in step (e) to from about 0° C. to about 4° C.

20. The method as set forth in claim 19 wherein said temperature is adjusted to about 2° C.

21. The method as set forth in claim 10 wherein said precipitate containing AHF is separated from said supernate solution by centrifugation or filtration.

22. A method of enhancing the solubility of AHF recovered from cryoprecipitated blood plasma or plasma fractions comprising adding polyethylene glycol (PEG) to said cryoprecipitated blood plasma during the recovery process in an amount which by itself is insufficient to precipitate the AHF.

23. A method of enhancing the solubility of AHF recovered from cryoprecipitated blood plasma or plasma fractions comprising adding polyethylene glycol (PEG) to said cryoprecipitated blood plasma during the recovery process wherein said recovery process is set forth in claim 10.

24. A method according to claim 23 wherein PEG is added during step (f) of the process.

25. The method as set forth in claim 24 wherein the amount of PEG added is in the range of from about 0.01 g % PEG to about 0.5 g %.

26. A method according to claim 22 wherein PEG is added between steps (c) and (d) of the process.

27. The method as set forth in claim 26 wherein PEG is added to bring the PEG concentration to from about 0.1 w/v % PEG to about 1.1 w/v % PEG.

28. The method as set forth in claim 27 wherein PEG is added to bring the PEG concentration to about 0.9 w/v % PEG.

29. The method as set forth in claim 1 wherein PEG is added between steps (c) and and (d) of claim 1.

30. The method as set forth in claim 29 where the amount of PEG added is from about 0.1 g % to about 0.6 g %.

31. The method of claim 30 wherein the amount of PEG added is about 0.5 g %.

32. A method according to claim 29 wherein the sodium concentration is adjusted in step (c) of the process to from about 150 mEq/liter to about 800 mEq/liter.

33. The method as set forth in claim 32 wherein said sodium concentration is adjusted to about 600 mEq/liter.

34. A method for increasing the solubility of an AHF preparation which comprises mixing said AHF preparation with a sufficient amount of polyethylene glycol (PEG) to increase the solubility of said AHF preparation.

35. The method as set forth in claim 34 wherein the amount of PEG added is sufficient to yield a concentration of from about 0.01 w/v % PEG to about 0.5 w/v % PEG.

36. The method as set forth in claim 35 wherein the amount of PEG added is sufficient to yield a concentration of about 0.1 w/v % PEG.

* * * * *